(12) United States Patent
Kan et al.

(10) Patent No.: US 11,229,616 B2
(45) Date of Patent: Jan. 25, 2022

(54) PHARMACEUTICAL COMPOSITION FOR CONTROLLED RELEASE OF TREPROSTINIL

(71) Applicants: Pharmosa Biopharm Inc., Taipei (TW); Pharmosa Therapeutics, Inc., Wilmington, DE (US)

(72) Inventors: Pei Kan, Taipei (TW); Yi Fong Lin, New Taipei (TW); Ko Chieh Chen, Taipei (TW)

(73) Assignee: PHARMOSA BIOPHARM INC., Taipei (TW)

( * ) Notice: Subject to any disclaimer, the term of this patent is extended or adjusted under 35 U.S.C. 154(b) by 0 days.

(21) Appl. No.: 16/404,272

(22) Filed: May 6, 2019

(65) Prior Publication Data

US 2019/0336461 A1 Nov. 7, 2019

Related U.S. Application Data

(60) Provisional application No. 62/667,889, filed on May 7, 2018, provisional application No. 62/670,875, filed on May 14, 2018.

(51) Int. Cl.
| | | |
|---|---|---|
| *A61K 9/00* | (2006.01) | |
| *A61P 11/00* | (2006.01) | |
| *A61K 31/192* | (2006.01) | |
| *A61K 47/28* | (2006.01) | |
| *A61K 9/127* | (2006.01) | |

(52) U.S. Cl.
CPC .......... *A61K 31/192* (2013.01); *A61K 9/0073* (2013.01); *A61K 9/1272* (2013.01); *A61K 47/28* (2013.01); *A61P 11/00* (2018.01)

(58) Field of Classification Search
None
See application file for complete search history.

(56) References Cited

U.S. PATENT DOCUMENTS

| | | | | |
|---|---|---|---|---|
| 5,192,549 A | * | 3/1993 | Barenolz | A61K 9/1278 264/4.1 |
| 5,939,096 A | | 8/1999 | Clerc et al. | |
| 2004/0156888 A1 | * | 8/2004 | Jensen | A61K 31/137 424/450 |
| 2010/0209538 A1 | | 8/2010 | Cipolla et al. | |
| 2011/0250266 A1 | * | 10/2011 | Barenholz | A61P 29/00 424/450 |
| 2015/0093434 A1 | | 4/2015 | Barenholz et al. | |
| 2016/0143868 A1 | * | 5/2016 | Olschewski | A61P 43/00 514/569 |
| 2019/0022004 A1 | | 1/2019 | Kan et al. | |
| 2019/0160009 A1 | | 5/2019 | Huang et al. | |

FOREIGN PATENT DOCUMENTS

| | | |
|---|---|---|
| TW | 201806585 A | 3/2018 |
| WO | 9625147 A1 | 8/1996 |
| WO | 2019023092 A1 | 1/2019 |

OTHER PUBLICATIONS

International Search Report and Written Opinion for PCT/US19/30841, dated Aug. 23, 2019.
Office action mailed in corresponding Taiwan application, dated Dec. 5, 2019.
Yuval Avnir et al., "Fabrication Principles and Their Contribution to the Superior In Vivo Therapeutic Efficacy of Nano-Liposomes Remote Loaded with Glucocorticoids," PLOS One, Oct. 2011, pp. e25721-e25721, vol. 6, issue 10.
Yechezkel (Chezy) Barenholz, "Doxil®—The first FDA-approved nano-drug: Lessons learned," Journal of Controlled Release, Mar. 2012, pp. 117-134, vol. 160.

* cited by examiner

*Primary Examiner* — Celeste A Roney
(74) *Attorney, Agent, or Firm* — Piloff Passino & Cosenza LLP; Sean A. Passino; Rachel K. Piloff

(57) ABSTRACT

Provided herein are pharmaceutical compositions containing (a) at least one liposome includes at least one vesicle-forming phospholipid; and (b) treprostinil encapsulated within the liposome. The ratio of treprostinil to phospholipid is equal to or higher than 0.035 and provides a controlled release of treprostinil. Also provided is the use of the pharmaceutical compositions to treat respiratory diseases.

18 Claims, 4 Drawing Sheets

PHARMACEUTICAL COMPOSITION FOR CONTROLLED RELEASE OF TREPROSTINIL

CROSS-REFERENCE TO RELATED APPLICATIONS

This application claims the benefit of U.S. Application No. 62/667,889 filed on 7 May 2018 and U.S. Application No. 62/670,875, filed on 14 May 2018, the entire disclosures of which are incorporated herein by reference.

FIELD

The present invention relates to a controlled release pharmaceutical composition of treprostinil, which is encapsulated in a liposome.

BACKGROUND

Liposomal compositions offer great potential for improving drug pharmacokinetics, such as enhanced blood circulation time, controlled drug release, reduced toxicity and targeted drug delivery.

A controlled or extended drug release profile is preferred to increase therapeutic efficacy. However, liposomal compositions with different controlled release profiles have distinctive disadvantages or deficiencies.

For example, the formation of insoluble drug precipitates, crystals or gels in the internal aqueous medium of the liposomes have been reported to overcome the problem of fast release or burst release of the encapsulated drug from a conventional liposome, whereby such burst release often causes side effects (Barenholz (2012), *Journal of Controlled Release,* 160:117-134 and U.S. Patent Publication Number US 2015/0093434 A1). However, such insoluble drug precipitates, crystals or gels do not provide adequate drug release or desired therapeutic efficacy and the drug may not be completely released from the liposome, causing drug accumulation in non-targeted tissues, potentially causing adverse side effects.

There remains a need for a liposomal composition without the burst release to reduce potential side effect but an extended release profile to sustain the therapeutic efficacy. The present invention addresses these and other needs.

BRIEF SUMMARY OF THE INVENTION

The present invention provides a pharmaceutical composition comprising one or more liposome suspended in an external medium, said liposome comprising (a) an external lipid bilayer, comprising at least one vesicle-forming phospholipid; and (b) an internal aqueous medium, comprising treprostinil and a salt which provides a pH gradient between the internal aqueous medium and the external medium, wherein the weight ratio of treprostinil to the at least one vesicle-forming phospholipid (i.e., T/P ratio) is equal to or higher than about 0.035 and about less than 60% of the treprostinil is released within 2 hours after the administration of the pharmaceutical composition and more than 80% of the treprostinil is released more than 2 hours to about 72 hours after the administration of the pharmaceutical composition.

The present invention also discloses a method of treating a respiratory disease, comprising the steps of administering the pharmaceutical composition described herein.

Also provided is a method for reducing the side effect of inhaled treprostinil in the upper respiratory track, comprising the step of administering to a subject in need thereof an effective amount of the pharmaceutical composition described herein.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following figures.

DETAILED DESCRIPTION

Figure 1A:
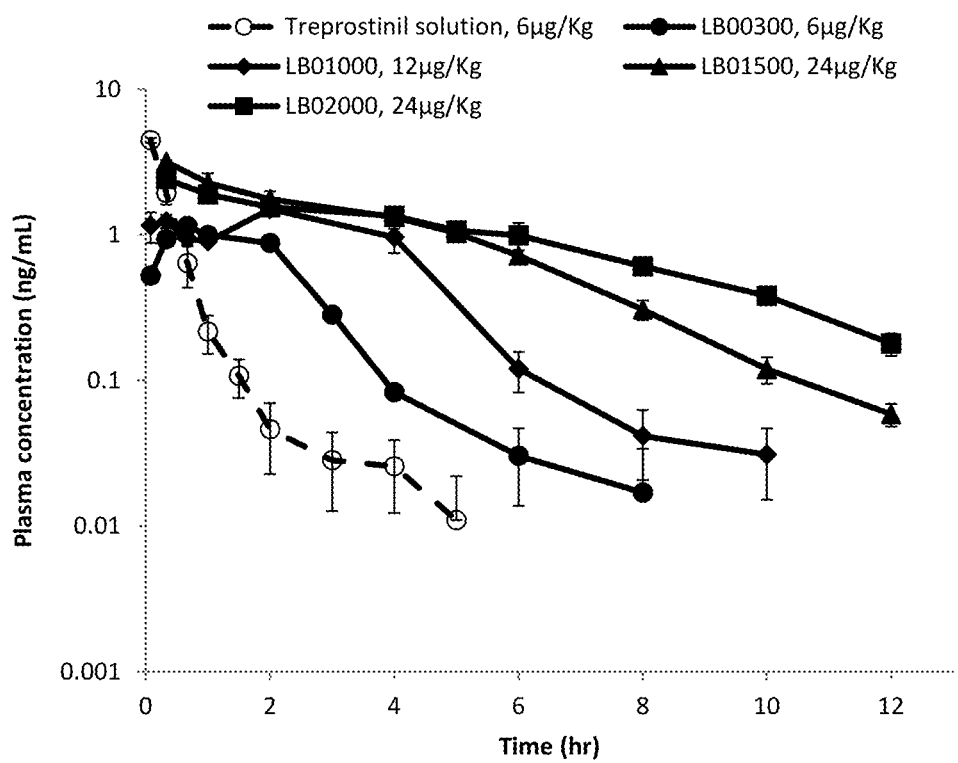
FIG. 1A and FIG. 1B are line graphs showing the log of mean plasma treprostinil concentration and the linear mean plasma treprostinil concentration of rats administered with free treprostinil solution and treprostinil-liposomal solutions of various T/P ratios.

As used herein, the articles "a" and "an" refer to one or more than one (i.e., at least one) of the grammatical object of the article. By way of example, "an element" means one element or more than one element.

All numbers are modified by the term "about". As used herein, the term "about" refers to a range of ±10% of a specified value.

The term "comprise" or "comprising" is generally used in the sense of include/including which means permitting the presence of one or more features, ingredients or components.

The term "subject" can refer to a vertebrate having a respiratory disease or to a vertebrate deemed to be in need of treatment for a respiratory disease. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

As used herein, the terms "encapsulation", "loaded" and "entrapped" can be used interchangeably, and refer to the incorporation or association of a biologically active agent (e.g., treprostinil) in the internal aqueous medium of a liposome.

The present disclosure provides a pharmaceutical composition containing one or more liposome suspended in an external medium, said liposome comprising: (a) an external lipid bilayer, comprising at least one vesicle-forming phospholipid; and (b) an internal aqueous medium, comprising treprostinil and a salt to provide a pH gradient between the internal aqueous medium and the external medium (hereafter "pH gradient salt"), wherein the weight ratio of treprostinil to the at least one vesicle-forming phospholipid (i.e., T/P ratio) is equal to or higher than about 0.035 and about less than 60% of the treprostinil is released within 2 hours after the administration of the pharmaceutical composition and more than 80% of the treprostinil is released more than 2 hours to about 72 hours after the administration of the pharmaceutical composition.

In an exemplary embodiment, the liposomes are suspended in an external medium and the pH of the external medium is above the $pK_a$ of treprostinil. In another exemplary embodiment, pH of the internal aqueous medium is at least 0.1 unit or at least 1 unit higher than the pH of the external medium. In yet another embodiment, the encapsulation efficiency of treprostinil is above about 80%, about 85%, about 90% or about 95%.

In one embodiment, the treprostinil-to-phospholipid ratio is equal to or higher than about 0.035, about 0.036, about 0.037, about 0.038, about 0.039, about 0.04, about 0.041, about 0.042, about 0.043, about 0.044, about 0.045, about 0.046, about 0.047, about 0.048, about 0.049, about 0.05, about 0.051, about 0.052, about 0.053, about 0.054, about 0.055, about 0.056, about 0.057, about 0.058, about 0.059 or about 0.06.

In another embodiment, the pharmaceutical composition reduces the burst release of treprostinil in the upper respiratory track (about less than 60% of the treprostinil is released within 2 hours after the administration), including the oral cavity, the nasopharynx and the larynx above the vocal cords. As a result, the side effects of the treprostinil in the upper respiratory track, such as cough, throat irritation, pharyngeal pain, epistaxis, hemoptysis and wheezing, are reduced compared to that of a pharmaceutical composition wherein the treprostinil-to-phospholipid ratio is lower than about 0.035. In yet another exemplary embodiment, the pharmaceutical composition extends the release of treprostinil from more than 2 hours to at least 4 hours, at least 6 hours, at least 8 hours, at least 10 hours, at least 12 hours at least 16 hours, at least 24 hours, at least 48 hours or at least 72 hours after the administration of the pharmaceutical composition (i.e., more than 80% of the treprostinil is released more than 2 hours to about 72 hours after the administration) and reduces the dosing frequency.

Also disclosed are methods for treating a respiratory disease comprising the step of administering to a subject in need thereof an effective amount of a pharmaceutical composition disclosed herein, wherein the treprostinil-to-phospholipid ratio of the pharmaceutical composition is equal to or higher than about 0.035 and side effect of treprostinil is reduced compared to that of a pharmaceutical composition with a treprostinil-to-phospholipid ratio of less than about 0.035. Non limiting examples of the respiratory disease include pulmonary hypertension and interstitial lung disease.

The present invention is also directed to methods for reducing the side effect of inhaled treprostinil in the upper respiratory track, comprising administering to a subject in need thereof an effective amount of a pharmaceutical composition disclosed herein, wherein the treprostinil-to-phospholipid ratio of the pharmaceutical composition is equal to or higher than about 0.035.

In some embodiments, the pharmaceutical composition disclosed herein is administered by inhalation and the burst release and the side effect of treprostinil is reduced compared to a pharmaceutical composition with a treprostinil-to-phospholipid ratio of less than about 0.035.

A. Liposomal Components

The term "liposome" as used herein refers to microscopic vesicles or particles made up of one or more lipid bilayers enclosing an internal aqueous medium. To form liposomes, the presence of at least one "vesicle-forming lipid" is needed, which is an amphipathic lipid capable of either forming or being incorporated into a lipid bilayer. Any suitable vesicle-forming lipid may be used to form the lipid bilayer constituting the liposomes. Vesicle-forming lipid includes, but not limited to, phospholipids such as phosphatidylcholine (PC), phosphatidylglycerol (PG), phosphatidylinositol (PI), phosphatidic acid (PA), phosphatidylethanolamine (PE) or phosphatidylserine (PS), and charged lipids, such as a positively charge lipid or a negatively charged lipid.

The lipid bilayer of the liposome includes at least one vesicle-forming lipid and a sterol, which is selected from the group consisting of cholesterol, cholesterol hexasuccinate, ergosterol, lanosterol, and any combination thereof, but is not limited thereto. In an exemplary embodiment, the sterol is cholesterol.

In some embodiments, the vesicle-forming lipid is a mixture of a first phospholipid and a second phospholipid. In certain embodiments, the first phospholipid is phosphatidylcholine (PC), which is selected from the group consisting of hydrogenated egg phosphatidylcholine (HEPC), hydrogenated soy phosphatidylcholine (HSPC), dipalmitoyl phosphatidylcholine (DPPC), distearyloyl phosphatidylcholine (DSPC), diarachidoyl phosphatidylcholine, dimyristoyl phosphatidylcholine (DMPC), egg phosphatidylcholine (EPC), soy phosphatidylcholine (SPC), oleoyl palmitoyl phosphatidylcholine, dioleoyl phosphatidylcholine (DOPC), dipetroselinoyl phosphatidylcholine, palmitoylelaidoyl phosphatidylcholine, palmitoyloleoyl phosphatidylcholine, dilauroyl phosphatidylcholine (DLPC), diundecanoyl phosphatidylcholine, didecanoyl phosphatidylcholine, dinonanoyl phosphatidylcholine, and any combination thereof. In other embodiments, the second phospholipid is a polyethylene glycol modified phospholipid, containing a polyethylene glycol having a molecular weight of about 500 to about 10,000 daltons, such as 1,2-distearoly-sn-glycero-3-phosphoethanolamine-N-[methoxy(polyethylene glycol)-2000](DSPE-PEG2000), a negatively charged phospholipid, such as distearyloyl phosphatidylglycerol (DSPG), Dipalmitoylphosphatidylglycerol (DPPG) or dimyristoylphosphatidylglycerol (DMPG) or (DOPG). In an exemplary embodiment, the mole percent of the first phospholipid:cholesterol:the second phospholipid is 50-70:20-45:0.1-10, 50-70:20-45:0.5-8 or 55-65:25-40:1-6.

In other embodiments, the vesicle-forming lipids are a mixture of a first phospholipid and a charged lipid. In an exemplary embodiment, vesicle-forming lipids are a mixture of a first phospholipid, a second phospholipid and a charged lipid. The charged lipid, includes stearylamine, 1,2-dioleoyl-3-trimethylammonium-propane (DOTAP), 3ß-[N—(N',N'-dimethylaminoethane)-carbamoyl]cholesterol (DC-Cholesterol), $N^4$—Cholesteryl-Spermine (GL67), dimethyldioctadecylammonium (DDAB), 1,2-di-O-octadecenyl-3-trimethylammonium propane (DOTMA), ethylphosphocholine (ethyl PC) or combination thereof. In another exemplary embodiment, the mole percent of the first phospholipid:cholesterol:charged lipid is 50-70:20-45:0.1-10, 50-70:20-45:0.5-8 or 55-65:25-40:1-6.

In an embodiment, the mole % of HSPC, cholesterol, and DSPG in the lipid bilayer is 50-70:20-45:0.1-10, 50-70:20-45:0.1-5 or 55-65:25-40:0.5-8. In another embodiment, the mole % of HSPC, cholesterol and DSPE-PEG2000 in the lipid bilayer is 50-70:20-45:0.1-10, 50-70:20-45:0.1-5 or 55-65:25-40:0.5-8. In another embodiment, the mole % of DPPC:Chol:DSPE-PEG2000 in the lipid bilayer is 50-70:20-45:0.5-8, 50-70:20-45:0.1-5 or 55-65:25-40:1-6.

In one embodiment, the lipid bilayer of the liposomes may also include at least one vesicle-forming lipid and a surfactant, which can be a non-ionic surfactant, a cationic surfactant or a zwitterionic surfactant. A non-ionic surfactant has no formally charged groups in its head. A cationic surfactant carries a net positive charge in its head. A zwitterion surfactant is electrically neutral but carries formal positive and negative charges on different atoms.

Non limiting examples of non-ionic surfactant include non-ionic water soluble mono-, di-, and tri-glycerides; non-ionic water soluble mono- and di-fatty acid esters of polyethyelene glycol; non-ionic water soluble sorbitan fatty acid esters (e.g. sorbitan monooleates such as TWEEN 20 (polyoxyethylene 20 sorbitan monooleate), SPAN 80); non-ionic water soluble triblock copolymers (e.g., poly(ethyleneoxide)/poly-(propyleneoxide)/poly(ethyleneoxide) triblock copolymers such as POLOXAMER 406 (PLURONIC F-127), or derivatives thereof.

Non-limiting examples of cationic surfactant include dimethyldialkylammonium bromide or dodecyltrimethylammonium bromide.

Non limiting examples of zwitterionic surfactant include 3-(N,N-dimethyl palmitylammonio)-propanesulfonate.

In some embodiments, the liposomes is substantially free of or detergent or an ionophore, which is a compound capable of facilitating the transport of $H^+$ or $OH^-$ across the liposome membrane.

A solvent for dissolving a vesicle-forming lipid for the preparation of liposomes can be used, for example, methanol, ethanol, ether, and combinations thereof. Optionally, the solvent can be removed by a supercritical fluid later, and is preferably used in a minimum amount so as to decrease the time for performing an organic solvent removing step.

According to the present invention, the liposomes are prepared in a medium containing a salt to provide a pH gradient between the internal aqueous medium and the external medium of the liposome (hereafter "pH gradient salt"). When the vesicle-forming lipid is in contact with a medium containing the pH gradient salt, a liposome suspension is formed.

The liposome in the suspension is subjected to size reduction. A liposome's size is typically referred to its diameter. Liposome size reduction can be accomplished by a number of methods, such as extrusion, sonication, homogenization techniques or milling techniques, which are well known and can be performed by persons skilled in this art. Extrusion includes passing liposomes, under pressure, one or more times through filters having defined pore sizes. The filters are generally made of polycarbonate, but can also be made of any durable material which does not interact with the liposomes and which is sufficiently strong to allow extrusion under sufficient pressure. The size of the liposomes can be reduced by sonication, which employs sonic energy to disrupt or shear liposomes that will spontaneously reform into smaller liposomes. For example, sonication can be conducted by immersing a glass tube containing the liposome suspension into the sonic epicenter produced in a bath-type sonicator, or a probe type sonicator may be used in which the sonic energy is generated by vibration of a titanium probe in direct contact with the liposome suspension. In the present invention, the liposomes generally have a diameter of about 50 nm to 500 nm, such as about 500 nm or less, about 400 nm or less, about 300 nm or less, about 200 nm or less or about 100 nm or less.

After sizing, the concentration of the pH gradient salt in the external medium is adjusted to provide a pH gradient between the internal aqueous medium and the external medium, which can be carried out by a number of ways, for example, by exchanging the external medium with a suitable buffer lacking the pH gradient salts such as citric acid buffer ($H_3C_6H_5O$) and phosphoric acid buffer ($H_3PO_4$), by methods such as diafiltration, dialysis, ultrafiltration, or tangential flow filtration.

The pH gradient salt provides a lower outside and a higher inside pH gradient between the external medium and the internal aqueous medium of the liposomes. In one embodiment, the pH of the internal aqueous medium is at least 0.1 unit higher than the pH of the external medium. In another embodiment, the pH of the internal aqueous medium is at least 1 unit higher than the pH of the external medium. In yet another embodiment, the pH of the internal aqueous medium is about 7, 8, 9 or 10 and the pH of the external medium is less than 7, less than 6, less than 5, less than 4, less than 3, about 3-7, about 3.5-6.5, or about 4-6. In yet another exemplary embodiment, the pH of the external medium is above the $pK_a$ of treprostinil.

The prepared liposome can be stored for substantial periods of time prior to treprostinil loading and administration to a subject. For example, liposomes can be stored at refrigerated conditions for substantial periods of time prior to treprostinil loading. Alternatively, liposomes can be dehydrated, stored, and subsequently rehydrated and loaded with treprostinil, prior to administration. Liposomes may also be dehydrated after being loaded with treprostinil. Dehydration can be performed by a number of methods available and known in the art. In some embodiments, liposomes are dehydrated using standard freeze-drying apparatus i.e. dehydration under low pressure conditions. Also, liposomes can be frozen e.g. using liquid nitrogen. Saccharides can be added to the liposomal environment, e.g., to the buffer containing the liposomes, prior to dehydration, to ensure stability and integrity of the liposome during dehydration. Examples of saccharides include but are not limited to maltose, lactose, sucrose, trehalose, dextrose, sorbitol, mannitol, xylitol, or a combination thereof.

A liposome suspension having a T/P ratio of equal to or higher than about 0.035 as described above are ready for treprostinil loading. Typically, treprostinil is added to the external medium of the liposome and the resultant suspension is incubated, allowing diffusion of treprostinil into the internal aqueous medium of the liposome and until a desired loading concentration and encapsulation efficiency (the percentage of the internal/encapsulated amount of treprostinil relative to the total amount of treprostinil in the composition) is achieved.

B. Amphiphilic Treprostinil

As used herein, the terms "amphiphilic treprostinil" and "treprostinil" can be used interchangeably, both refer to a biologically active treprostinil intended for loading into liposome and also contain at least one functional group selected from the group consisting of a carboxyl group (—COOH) and a hydroxyl group (—OH), which is mostly soluble without forming insoluble crystals, precipitates or gels and is stable in alkaline solution. Treprostinil may also contain one or more functional groups in addition to the carboxylic functionality, although the presence of such functional group should not significantly alter the acidity of treprostinil from that of its nonfunctionalized counterpart.

According to the present disclosure, the amphiphilic treprostinil may be biologically active in its protonated form or any salt forms thereof. A salt of an amphiphilic treprostinil may be accompanied by any pharmaceutically acceptable counterion which is in an aqueous soluble form.

In one embodiment, the amphiphilic treprostinil is treprostinil.

C. Association Between Treprostinil to Phospholipid Ratio and Controlled Release Profile According to the present disclosure, a pH gradient salt is used to provide a pH gradient between the intra- and extra-liposomal compartments and allow the loading of treprostinil into the internal aqueous medium, and not entrapped within the liposomal membrane or associated with external surface of the lipid bilayer.

Non limiting examples of pH gradient salt include a weak acid salt (such as carboxylic acid salt or bicarbonate salt) or an amino acid (such as a polar amino acid).

"Bicarbonate salt" as used herein refers to a pharmaceutically acceptable salt compound including a bicarbonate anion and a cationic component. In one embodiment, the cationic component of the salt compound is a metal. Non-limiting examples of the metal include a Group IA or IIA metal, such as potassium (K), sodium (Na), calcium (Ca), magnesium (Mg), cesium (Cs), and lithium (Li) or a metal other than Group IA or IIA metal, such as ferrous iron (Fe) and nickel (Ni). Examples of bicarbonate salt include, but not limited to, potassium bicarbonate, sodium bicarbonate, calcium bicarbonate, magnesium bicarbonate, cesium bicarbonate, lithium bicarbonate, nickel bicarbonate, ferrous iron bicarbonate or any combination thereof.

"Carboxylic acid salt" as used herein includes, but not limited to, formate, acetate, propionate, butyrate, isobutyrate, valerate, isovalerate or a combination thereof. In one exemplary embodiment, the acetate is sodium acetate, calcium acetate, or a combination thereof

TABLE 1

| | | | | |
|---|---|---|---|---|
| Non-polar | | Glycine | Isoleucine | Phenylalanine |
| | | Alanine | Valine | Methionine |
| | | Leucine | Proline | Tryptophan |
| Polar | Acidic | Asparate | | Glutamate |
| | Neutral | Tyrosine | Serine | Asparagine |
| | | Glutamine | Threonine | Cysteine |
| | Basic | Histidine | Lysine | Arginine |

Table. 1 shows the classification of 20 amino acids. The 20 amino acids are classified according to Juang R H (2007) Biochemistry. In one embodiment, the pH gradient salt is a polar amino acid, including a neutral polar amino acid (Tyrosine, Asparagine, Glutamine, Cysteine, Serine, Threonine), a basic polar amino acid (Arginine, Lysine, Histidine), an acidic polar amino acid (Aspartate, Glutamate) or a combination thereof.

In certain embodiments, the pH gradient salt is not phosphate. In an exemplary embodiment, the pH gradient salt is bicarbonate. In another exemplary embodiment, the pH gradient salt is acetate.

A counter ion is selected to accompany the pH gradient salt to maintain a stable pH gradient such that the interaction between the counter ion with the pH gradient salt together achieve the optimal effect of the pH gradient salt, i.e., encapsulating a high concentration of treprostinil in the internal aqueous medium of the liposome and/or extending the release rate of the same from the liposome. It will be appreciated that after the pH gradient is established, excess counter ions within the liposome provide a wealth of hydroxide and these counter ions alone are membrane-impermeant. Treprostinil in its neutral form can permeate the lipid bilayer under the incubation conditions during liposome loading, and de-protonates in response to the counter ions. The de-protonated treprostinil does not readily permeate across the liposome bilayer. In certain embodiments, the counter ion may be an ion of alkali metals.

In certain embodiment, the internal aqueous medium is substantially free of precipitates, crystals or gels. The internal aqueous medium is considered to be substantially free of precipitates, crystals or gels if no such precipitates, crystals or gels are visible on electron microscopy with at least 5000×, 8000×, 10000×, 12000×, 15000× or 20000× magnification.

The pharmaceutical compositions of the present invention having a specific range of a treprostinil-to-phospholipid ratio reduces the burst release of the encapsulated treprostinil and hence reduce the side effect of the treprostinil. Furthermore, sufficient amount of treprostinil for a desired therapeutic effect is released from the pharmaceutical composition and the release profile is extended compared to that of the pharmaceutical composition with the treprostinil-to-phospholipid ratio falling outside the specific range of this disclosure. This claimed treprostinil-to-phospholipid ratio unexpectedly extends the release of the entrapped treprostinil from the liposomal composition while reducing the side effects of treprostinil, without the use of a detergent or an ionophore (such as calcium ionophore) for the release profile described herein.

As used herein, the term "burst release" refers to rapid and/or somewhat uncontrolled release of >60% of treprostinil from the pharmaceutical composition within 2 hours of administration of the pharmaceutical composition. In certain embodiments, the burst release of the treprostinil of the pharmaceutical composition disclosed herein is reduced, so less than about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39% or about 38% of the encapsulated treprostinil is released within about 2 hours of drug administration.

As used herein, the term "extended release" can be used interchangeably with "controlled release", "delayed release", "modified release", "prolonged release", "programmed release", "time release", "rate controlled" or "sustained release". and refers to the release of more than 80% of treprostinil during a period of more than 2 hours to about 72 hours after the administration of the pharmaceutical composition.

In one embodiment, the sustained release profile of the pharmaceutical composition is based on the in vitro release (IVR) assay and/or the in vivo pharmacokinetics study of entrapped treprostinil.

In certain embodiments, based on in vitro release (IVR) assay and/or the in vivo pharmacokinetics study, the pharmaceutical composition has a release profile wherein less than about 60%, 55%, 50%, 45%, 40% or 35% by weight of the entrapped treprostinil is released within 2 hours from the time of drug administration.

In certain embodiments, based on in vitro release (IVR) assay and/or the in vivo pharmacokinetics study, the pharmaceutical composition has a release profile wherein more than about 90%, 85%, 80%, 75%, 70%, 65%, 60% or 55% by weight of the entrapped treprostinil is released from the liposome, more than 2 hours to 4 hours, 8 hours, 12 hours, 24 hours, 48 hours, or 72 hours from the time of drug administration.

D. Administration

The pharmaceutical composition of the present invention may be administered into a cavity of a subject that does not have a direct contact with the bloodstream. Examples of the routes of administration include, but are not limited to, inhalation, intratracheal injection, subcutaneous injection, intraarticular injection, intramuscular injection, intravitreal injection and intrathecal injection.

In certain embodiments, the pharmaceutical composition may be administered via intratracheal injection. In some embodiments, the pharmaceutical composition may be administered via subcutaneous injection.

The pharmaceutical composition of the present invention may also be administered directly into the bloodstream of a subject.

According to this disclosure, the pharmaceutical composition may be administrated once to three times a day, once every 2 days or once every 3 days.

The present disclosure will be further described in the following examples. However, it should be understood that the following examples are solely intended for the purpose of illustration and should not be construed as limiting the present disclosure in practice.

EXAMPLES

General Experimental Procedures:
1. Preparation of Treprostinil Liposomal Composition A liposomal colloidal suspension was prepared using ethanol injection technique. To be specific, all lipid ingredients including a first phospholipid (i.e., HSPC), cholesterol and a second phospholipid (i.e., DSPE-PEG2000) at a molar ratio of 3:2:0.075 were dissolved in 2.86 mL of ethanol solution at approximately 60° C. The resultant lipid solution was then injected into 17.14 mL of sodium bicarbonate solution (400 mM; pH 8.5) and was stirred at 60° C. for liposome hydration. The mixture was extruded 6 to 10 times through polycarbonate membranes with specific pore sizes (0.2 and/or 0.1 μm, respectively), to obtain a suspension of liposomes having a mean particle size around 100 nm to 200 nm and a polydispersity index (PdI) of <0.2. Subsequently, the suspension of liposomes was dialyzed with a tangential flow filtration system against 50 mM of sodium citrate buffer (pH 5.5) to form a transmembrane pH gradient between the internal aqueous medium of the liposome and the external medium (i.e., a higher inside and lower outside pH gradient). The suspension of liposomes with transmembrane pH gradient was stored at 4° C. before drug loading process.

Treprostinil (purchased from Cayman Chemical, USA) was dissolved in 50 mM of sodium citrate aqueous solution, then added into the suspension of liposomes at a given treprostinil-to-phospholipid ratio and incubated at 40° C. for 30 min. The resultant mixture was adjusted with sodium citrate buffer (pH 5.5) to obtain a treprostinil liposomal composition having a pH of 5.5 and a phospholipid concentration of 8.59 mg/mL.

General Analysis Method:

1. Quantitative Characterization of Treprostinil Liposomal Composition a. Concentrations of Encapsulated and Free Treprostinil:

The treprostinil liposomal composition was poured into a PD MiniTrap™ G-25 column (GE Healthcare) to separate treprostinil-loaded liposome (i.e., the encapsulated treprostinil within the liposome) from free treprostinil (i.e., outside the liposome).

The treprostinil-liposomal composition was damaged using methanol (90% methanol and 10% liposome suspension), the concentration of the encapsulated treprostinil and the concentration of free treprostinil (outside the liposome) were respectively analyzed quantitatively by injecting the above test sample solution (20 μL) into a Waters Acquity HPLC system equipped with a photodiode array (PDA) detector. The mobile phase is a mixture of acetonitrile and phosphate buffer (pH 2.5) (50:50, v/v), and the flow rate of the mobile phase is 1.0 mL/min. Separation was performed using C18 Column, having a dimension of 4.6 mm×15 cm, 5 μm, at 45° C. and absorbance peak was detected at 220 nm.

The concentration of total amount of treprostinil in the treprostinil liposomal composition, which includes the encapsulated treprostinil in internal aqueous medium (L) and the free treprostinil in the external medium (F), is represented by [TRE].

b. Encapsulation Efficiency (EE) and Treprostinil-to-Phospholipid (T/P) Ratio:

Encapsulation efficiency (EE) was calculated as the percentage of the encapsulated treprostinil in the internal aqueous medium of the liposome (L) relative to the total amount of the treprostinil [TRE] (i.e., the sum of encapsulated treprostinil (L) and free (non-encapsulated) treprostinil in the external medium (F)). In other words, the EE was calculated using the following formula:

$$EE\ (\%) = [L/(L+F)] \times 100$$

T/P ratio of the treprostinil liposomal composition was calculated using the following formula:

$$T/P\ \text{ratio} = (B \times C)/D$$

B=the concentration of the total amount of treprostinil (L+F)=[TRE] (mg/mL)

C=the encapsulation efficiency (EE)

D=the phospholipid concentration.

c. Mean Particle Size and Polydispersity Index (PdI):

The mean particle size of the liposome was evaluated by dynamic light scattering. The polydispersity index (PdI), a value indicating the size distribution of the liposomes, was determined using the same evaluation technique as for the mean particle size, using Beckman Coulter Delsa™ Nano C particle analyzer.

Example 1. In Vitro Release (IVR) Profile and In Vivo Pharmacokinetics (PK) Profile of Treprostinil Liposomal Compositions Using Bicarbonate Salt with Different Treprostinil-to-Phospholipid (T/P) Ratio Experimental Procedures:

A. In Vitro Release (IVR) Assay

To study the effect of treprostinil-to-phospholipid ratio on the release of the encapsulated treprostinil, treprostinil liposomal compositions formulated with HSPC, cholesterol and DSPE-PEG2000 with specific treprostinil-to-phospholipid ratios as shown in Table 2 were prepared according to the procedures as described in the preceding section, entitled "1. Preparation of treprostinil liposomal composition," of the General Experimental Procedures. The mean particle size of the liposome is 100-200 nm and the PdI was less than 0.20

Quantitative characterization of the treprostinil liposomal compositions, including the concentrations of the encapsulated and free treprostinil, encapsulation efficiency, treprostinil-to-phospholipid ratio, mean particle size and PdI, were carried out according to the procedures as described in the preceding section, entitled "1. Quantitative characterization of treprostinil liposomal composition," of the General Analysis Method.

Various IVR assays can be used to assess the IVR profile. The actual IVR assay is known, or will be apparent, to those skilled in the art depending on the treprostinil in the claimed liposomal composition. The IVR profile of treprostinil was assessed by the IVR assay according to M. R. C. Marques et al. (2011), Dissolution Technologies, 18:15-28. Briefly, 0.5 mL of a release medium was prepared according to M. R. C. Marques et al. (2011) and added into a 20 kDa cellulose ester membrane dialysis tube (Cat. No. 88405, Thermo Fisher Scientific), and the cellulose ester membrane dialysis tube was then placed in a 15-mL screw cap conical tube containing 14 mL of the release medium. Non limiting example of the release medium includes simulated lung fluid (SLF).

A suitable amount of the treprostinil liposomal composition was added into the conical tube to obtain a final concentration of 5 µg/mL of treprostinil, followed by dialysis at 37° C. and 100 rpm. At a predetermined time point (i.e., 0, 2, 4, 8, 12, 24, 48 and 72 hours post dialysis), about 0.5 mL of the mixture in the dialysis tube was taken out to measure the concentration of treprostinil released from the liposome into the dialysis tube using HPLC according to the procedures described in the preceding section.

The percentage of the encapsulated treprostinil released from the SLF is calculated using Equation 1.

$$\text{Release } (\%)_{at\ t} = \frac{C_{Release\ at\ t}}{C_{Encap\ at\ t_0}} = \frac{C_{Non-encap\ at\ t} - C_{Non-encap\ at\ t_0}}{C_{Encap\ at\ t_0}} \quad \text{Equation 1}$$

$$= \frac{(C_{Non-encap\ at\ t})_{diffuse\ at\ t} - (C_{Non-encap\ at\ t_0})_{diffuse\ at\ t}}{(C_{Encap\ at\ t_0})_{diffuse\ at\ t}}.$$

wherein:

$C_{Release\ at\ t}$ (µg/mL): The concentration of treprostinil released from liposomal composition at a specific time (t, sec)

$C_{Encap\ at\ t0}$ (µg/mL): Initial ($t_0$) concentration of encapsulated treprostinil of liposomal composition $C_{Non-encap\ at\ t0}$ (µg/mL): Initial ($t_0$) concentration of non-encapsulated treprostinil of liposomal composition $C_{Non-encap\ at\ t}$ (µg/mL): The concentration of non-encapsulated treprostinil of liposomal composition at a specific time (t, sec)

$(C_{Non-encap\ at\ t})_{diffuse\ at\ t}$: The measured concentration of non-encapsulated treprostinil of liposomal composition that diffuse through dialysis membrane at a specific time (t, sec)

$(C_{Non-encap\ at\ t0})_{diffuse\ at\ t}$: The estimated initial ($t_0$) concentration of non-encapsulated treprostinil of liposomal composition that diffuse through dialysis membrane at a specific time (t, sec)

$(C_{Encap\ at\ t0})_{diffuse\ at\ t}$: The estimated initial (to) concentration of encapsulated treprostinil that diffuse through dialysis membrane at a specific time (t, sec).

in which, $(C_{Non-encap\ at\ t0})_{diffuse\ at\ t}$ was calculated using Equations 1-(1) and 1-(2), and $(C_{Encap\ at\ t0})_{diffuse\ at\ t}$ was calculated using the Equations 1-(3) and 1-(4) as follows:

$$(C_{Non-encap\ at\ t_0})_{diffuse\ at\ t} = C_{max} - (C_{max} - C_0) \cdot e^{-D \cdot (t-t_0)}. \quad \text{Equation 1-(1)}$$

$$C_{max} = \frac{(C_{Release\ medium} \times (1 - EE\ \%)) \times 14\ [\text{mL}]}{14.5\ [\text{mL}]}. \quad \text{Equation 1-(2)}$$

$$(C_{Encap\ at\ t_0})_{diffuse\ at\ t} = C_{max} - (C_{max} - C_0) \cdot e^{-D \cdot (t-t_0)}. \quad \text{Equation 1-(3)}$$

$$C_{max} = \frac{(C_{Release\ medium} \times EE\ \%) \times 14\ [\text{mL}]}{14.5\ [\text{mL}]}. \quad \text{Equation 1-(4)}$$

wherein, $C_{release\ medium}$ (µg/mL): The initial concentration of treprostinil in the release medium EE (%): The encapsulation efficiency of treprostinil in the liposome The diffusion coefficient (D) of treprostinil that diffuse through the dialysis membrane was assessed primarily by the free form of treprostinil that is dissolved in the release medium. Assuming the diffusion of treprostinil obeys Fick's law (Equation 1), the concentration of diffused treprostinil across the dialysis membrane increased in an exponential manner within a specific time period and can be calculated using Equation 2.

$$C_t = C_{max} - (C_{max} - C_0) \cdot e^{-D \cdot (t-t_0)}. \quad \text{Equation 2}$$

$$\ln \frac{(C_{max} - C_t)}{(C_{max} - C_0)} = -D \times (t - t_0).$$

wherein, $C_t$ (µg/mL): The concentration of treprostinil that diffuse across dialysis membrane at a specific time (t, sec)

$C_{max}$ (µg/mL): The concentration of treprostinil that diffuse across dialysis membrane while in equilibrium $C_0$ (µg/mL): The initial (to) concentration of treprostinil in dialysis membrane (5 µg/mL)

Results:

Physicochemical characterization and IVR profile of the treprostinil liposomal compositions with different T/P ratios are shown in Table 2.

TABLE 2

| Composition | [TRE] (mg/mL) | EE(%) | T/P ratio | Release(%) in SLF (Reverse dialysis) | | | | | |
|---|---|---|---|---|---|---|---|---|---|
| | | | | 0 h | 2 h | 4 h | 8 h | 12 h | 24 h |
| LB00300 | 0.29 | 96.2 | 0.032-0.033 | 0 | 63.8 | 79.9 | 93.9 | N.A | N.A. |
| LB00400 | 0.40 | 99.9 | 0.047 | 0 | 46.3 | 72.7 | 94.3 | N.A. | N.A. |
| LB00500 | 0.53 | 91.2 | 0.056 | 0 | 37.0 | 54.6 | 84.5 | N.A. | N.A. |
| LB01000 | 0.99 | 97.6 | 0.112 | 0 | 26.3 | 47.4 | 72.2 | 82.8 | N.A. |
| LB01500 | 1.57 | 96.7 | 0.177 | 0 | 20.5 | 40.0 | 64.5 | 74.6 | 94.1 |
| LB02000[b] | 2.12 | 91.0 | 0.225 | 0 | 14.1 | 33.0 | 51.2 | 62.8 | 81.3[a] |

[a] The data was calculated by nature log fitting (release (%) = 21.041 × Ln (time, hr) − 4.639)
[b] mean particle size of liposome: 180-200 nm, PdI < 0.20

Table 2 shows >90% EE was achieved with a sodium bicarbonate salt. Treprostinil liposomal compositions in Table 2 with a T/P ratio that is higher than 0.035 (i.e., LB00400, LB00500, LB01000, LB01500 and LB02000) show the controlled in vitro release of the following characteristics: less than 60% of the treprostinil is released within 2 hours from the time of administration and more than 80% of the treprostinil is released more than 2 hours to within 24 hours from the time of administration (i.e. 8 hr, 12 hr or 24 hr), when compared with compositions having a T/P ratio lower than 0.035 (i.e. LB00300).

B. In Vivo Pharmacokinetics (PK) Study of Treprostinil Liposomal Compositions

Experimental Procedures:

In this in vivo PK study, Sprague-Dawley rats (purchased from BioLASCO Taiwan Co., Ltd.) were anaesthetized with isoflurane, and positioned securely on its back to an arched platform in a dorsal position at a 45° to 50° plane using a ribbon hooked around upper incisors. A microspray aerosol tip (Microsprayer, PennCentury, Philadelphia, USA) was inserted to the tracheal bifurcation of each rat, and a test sample (i.e., compositions in Table 2 or free treprostinil solution) was administered intra-tracheally to each rat at a given dose using a high-pressure syringe that is attached to the microspray aerosol device. The free treprostinil solution was prepared by dissolving 6 mg of treprostinil in 50 mM of sodium citrate aqueous solution and then bring up to 10 mL with 0.9% saline.

At a predetermined time point (i.e., 0, 0.25, 0.5, 0.75, 1, 2, 3, 4, 5, 6, 8, 10 and 12 hours post administration), a blood sample of each rat was collected into a heparin-containing tube and maintained on wet ice. The blood sample was then centrifuged at approximately 2500×g for 15 min and at 4±2° C. within 1 hour of collection, so as to separate the plasma from the blood cells. Approximately 0.1 mL of the obtained plasma sample from each rat was added into a new storage tube and stored in a freezer with a temperature maintained at −70±2° C.

For quantification of treprostinil concentration, 50 µL of the plasma sample of each rat was transferred into a well of a 96-wells plate, followed by addition of 150 µL of acetone nitrate to each well. The resultant mixture was vortexed for 1 minute to disrupt the binding of plasma proteins to treprostinil, followed by centrifugation at 3000 rpm for 5 minutes. The obtained supernatant (150 µL) was mixed with an equal volume of $H_2O$ and analyzed by liquid chromatography-tandem mass spectrometry (LC-MS/MS) to determine the treprostinil concentration in the plasma sample of the rat.

Figure 1B:
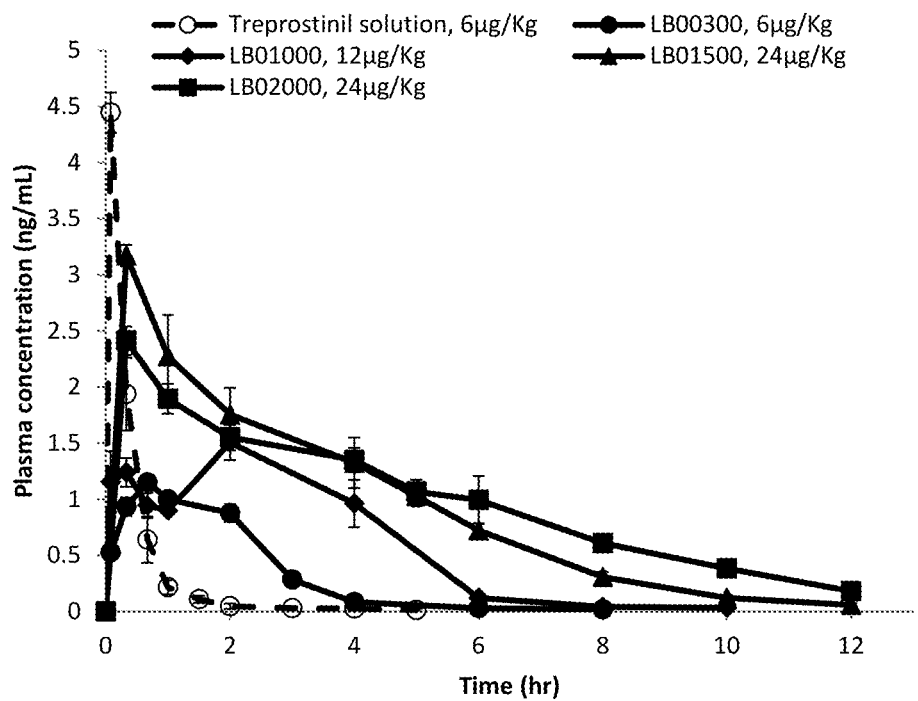

The log of mean treprostinil concentration and the linear mean treprostinil concentration in the plasma samples of the rats administered with various test samples at a given dose versus administration time of up to 12 hours were respectively plotted as shown in FIGS. 1A and 1B.

Figure 2:
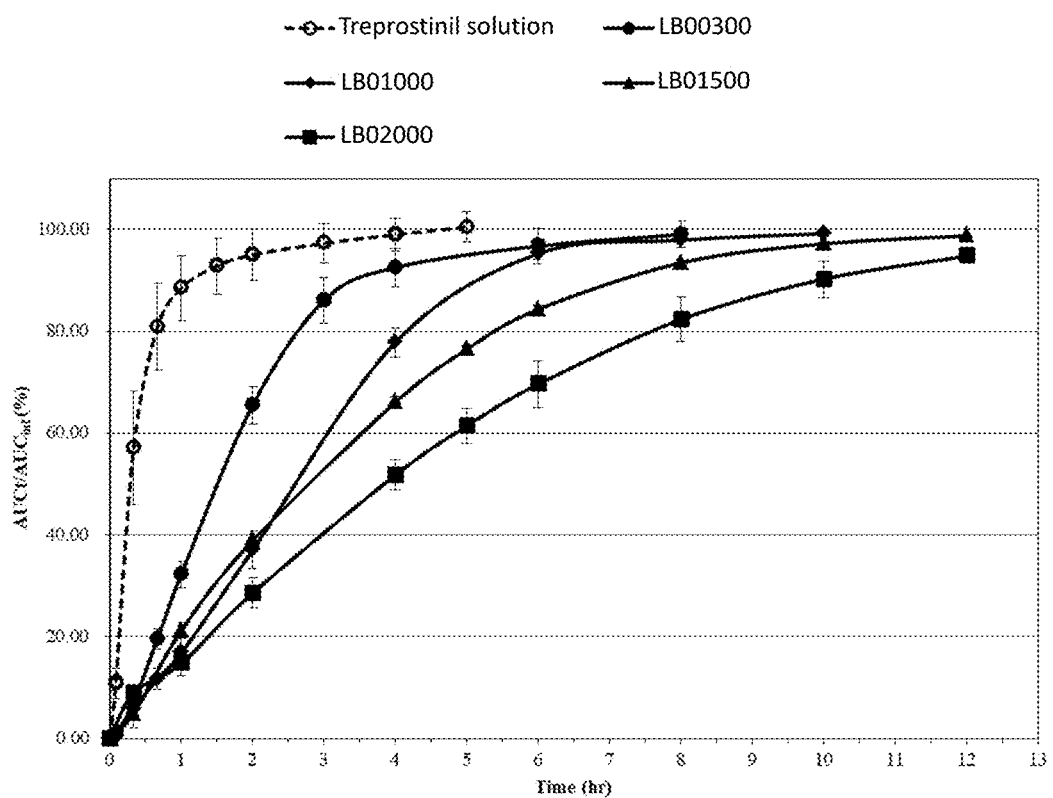
FIG. 2 is a line graph illustrating the ratio of area under the plasma concentration-time curve from time zero to specific time ($AUC_t$) to area under the plasma concentration-time curve from time zero to infinity ($AUC_{inf}$).

For the purpose of determining total exposure of treprostinil over a time period and for normalizing different dosage of treprostinil used in each test sample, the ratio of area under the plasma concentration-time curve from time zero to specific time ($AUC_t$) to area under the plasma concentration-time curve from time zero to infinity ($AUC_{inf}$) is shown in FIG. 2.

Results:

As shown in FIGS. 1A and 1B, plasma treprostinil concentration peaked within the first 5 minutes of free treprostinil administration. No significant peak was noted after the administration of treprostinil liposomal compositions (i.e. LB00300, LB01000, LB01500, and LB02000). As shown in FIG. 2, >60% of treprostinil ($AUC_t/AUC_{inf}$) was released within 2 hours in free treprostinil and LB00300 (T/P<0.035) administration, indicates a burst release.

The LB01000, LB01500 and LB02000 tresprostinil-liposomal compositions, all of which have a T/P ratio greater than 0.035, showed a sustain release profile (>80% $AUC_t/AUC_{inf}$ occurred more than 2 hour to about 72 hour after administration) and without a burst release (i.e. the $AUC_t/AUC_{inf}$<60% within 2 hour of administration).

This study shows treprostinil-liposomal compositions with T/P ratio equal to or greater than 0.035 have the following characteristics:

(a) no burst release of treprostinil and hence, reduced side effects;

(b) treprostinil plasma level remained constant with little fluctuation to achieve a stable therapeutic window; and (c) extended release for a longer period of time.

Example 2. IVR Profile of Treprostinil Liposomal Compositions with Different Vesicle-Forming Phospholipids Experimental Procedures:

An in vitro study was performed to investigate the effect of liposomal phospholipid on the release profile of treprostinil. The treprostinil liposomal compositions in this study were prepared according to the procedures as described in the preceding section entitled "1. Preparation of treprostinil liposomal composition" and analyzed according to the procedures as described in the preceding section entitled "1. Quantitative characterization of treprostinil liposomal composition". The IVR profile of the treprostinil liposomal compositions was determined according to the procedures as described in Example 1, entitled "A. In vitro release (IVR) assay" of the Experimental Procedures.

Results:

The physicochemical characterization and IVR profile of various treprostinil liposomal compositions are shown in Table 3.

TABLE 3

| Composition | Second phospholipid | [TRE] (mg/mL) | EE(%) | T/P ratio | Release(%) in SLF (Reverse dialysis) | | | | | |
|---|---|---|---|---|---|---|---|---|---|---|
| | | | | | 0 h | 2 h | 4 h | 8 h | 12 h | 24 h |
| LB01000 | DSPE-PEG2000 | 0.99 | 97.6 | 0.112 | 0 | 26.3 | 47.4 | 72.2 | 82.8 | N.A |
| LB01500 | | 1.57 | 96.7 | 0.177 | 0 | 20.5 | 40.0 | 64.5 | 74.6 | 94.1 |
| LB11000 | DSPG | 1.04 | 95.7 | 0.123 | 0 | 29.3 | 47.8 | 76.8 | 85.2 | N.A |
| LB11500 | | 1.56 | 95.1 | 0.183 | 0 | 23.0 | 43.5 | 68.6 | 79.5 | 93.9 |

N.A.: Non available

As shown in Table 3, treprostinil liposomal compositions comprising DSPG phospholipid (i.e., LB11000 and LB11500) or DSPE-PEG2000 phospholipid (i.e., LB01000 and LB01500) show similar IVR profiles (less than 60% of the treprostinil is released within 2 hours from the time of administration and more than 80% of the treprostinil is released more than 2 hours to within 72 hours (i.e. 12 hr or 24 hr) from the time of administration).

Example 3. IVR Profile of Treprostinil Liposomal Compositions with Different Salt Solutions Experimental Procedures:
An in vitro study was carried out to study the effect of different salts on the IVR profile of treprostinil liposomal compositions. The liposomal compositions of this study were prepared and the IVR profiles were analyzed according to the procedures outlined in Example 1.

Three weak acid salt solutions were used to load treprostinil in this example: sodium bicarbonate solution (400 mM; pH 8.5), sodium acetate solution (400 mM; pH 8.5) and sodium phosphate solution (400 mM; pH 8.5).

Results:
The physicochemical characterization and IVR profile of treprostinil liposomal compositions using different salts are shown in Table 4.

TABLE 4

| Composition | Buffer salt solution | [TRE] (mg/mL) | EE (%) | D/L ratio | Release (%) in SLF (Reverse dialysis) | | | | | |
|---|---|---|---|---|---|---|---|---|---|---|
| | | | | | 0 h | 2 h | 4 h | 6 h | 8 h | 12 h |
| LB01000 | Bicarbonate | 0.99 | 97.6 | 0.112 | 0 | 26.3 | 47.4 | N.A. | 72.2 | 82.8 |
| LA01000 | Acetate | 1.01 | 91.0 | 0.107 | 0 | 31.1 | 46.7 | N.A. | 75.8 | 87.3 |
| LP00100 | Phosphate | 0.10 | 94.5 | 0.011 | 0 | 73.4 | 75.7 | 83.6 | N.A. | 90.6 |

Table 4 shows no burst release (less than 60% of the treprostinil is released within 2 hours from the time of administration) and extended IVR profile (more than 80% of the treprostinil is released more than 2 hours to within 72 hours (i.e. 12 hr) from the time of administration) was achieved with bicarbonate and acetate salts, but not phosphate salt. Without being bound by any particular theory, it is believed that bicarbonate and acetate ions can permeate across the lipid bilayer to achieve adequate transmembrane pH gradient between the internal aqueous medium and exterior of the liposome for loading treprostinil, whereas phosphate ions cannot generate sufficient transmembrane pH gradient (as phosphate is impermeable across the lipid bilayer), hence T/P ratio was less than 0.035 and limited the loading of treprostinil.

The above results suggest that transmembrane pH gradient of the liposome generated by bicarbonate and acetate salts (but not phosphate salt) is important to achieve the T/P ratio not less than 0.035, reduce burst release and the controlled or extended IVR profile.

Example 4. Safety Evaluation of Inhaled Treprostinil Liposomal Composition

Experimental Procedures:
In this study, 8 male Sprague Dawley rats (purchased from BioLASCO Taiwan Co., Ltd.) were divided into 3 groups: control group (n=2), comparative group (n=3) and experimental group (n=3). The experimental group rats and the comparative group rats were placed in restraining tubes and given nebulized treprostinil liposomal composition LB11500 from Example 2 and free treprostinil solution, respectively, at a dosage of 6 µg/kg/day for 10 days, via a 20-port nose-only Buxco inhalation exposure system (DSI, USA). An air flow carried aerosol generated by mesh vibrating nebulizer was provided to the system tower where the rats are encased in, at a rate of 10 L/min. The control group rats received no exposure to the drug.

During the study, cage-side clinical observation was performed on each rat by a single observer to record incidences of upper airway irritation due to the inhaled nebulized treprostinil liposomal composition or free treprostinil solution. Manifestations of upper airway irritation include tension, sneezing, erythematous pinnae, tremor, hunched posture, piloerection, tachypnea and labored breathing, hyperpnea and epistaxis.

Results:
Table 5 shows the incidence of upper airway irritation recorded in each group of rats.

TABLE 5

| Groups | Incidences[1] of upper airway irritation |
|---|---|
| Control group (n = 2) | 0 |
| Experimental group/treprostinil liposomal composition LB11500 (n = 3) | 5 |
| Comparative group/free treprostinil solution (n = 3) | 17 |

[1]Incidence is denoted the frequency of clinical signs in 10 inhalations.

This study demonstrates an exemplary embodiment of the treprostinil liposomal compositions of the present invention induces less upper respiratory track irritation than that of free treprostinil solution.

Example 5. The IVR Profile and Precipitation Status of Treprostinil Liposomal Compositions with Different Drugs and Different Weak Acid Salts Liposomal compositions comprising HSPC:Cholesterol:PEG2000-DSPE at a molar ratio of 3:2:0.075 were prepared according to the procedures outline in Example 1. The mean particle size of liposome was 100-140 nm and PdI was less than 0.20. Treprostinil (TRE), MRE-269 or Iloprost was loaded into the liposomal composition using calcium acetate ($Ca(AC)_2$), sodium acetate (NaAC) or sodium bicarbonate (NaBic).

The methylprednisolone sodium succinate (MPS) liposomal composition was prepared according to the procedures in Barenholz et al. (2012), *Journal of Controlled Release*, 160:117-134.

The IVR profiles of the liposomal compositions were assessed using the procedures described in Example 1. The presence of precipitation in the internal aqueous medium of the liposomes was assessed by Cryo-transmission electron microscope (Cryo-TEM), using an JEOL JEM-2100 electron microscope, operating at 200 keV equipped with CCD Gatan 832 (4 k×2 k) camera. Vitreous ice grids were transferred into the electron microscope using a cryostage that maintains the grids at a temperature below −170° C. The Cryo-TEM images were acquired at LOW-Dose model, providing a magnification of 20000× (0.30 nm/pixel).

Results:

Table 6 shows the physicochemical characterization, IVR profile and the presence or absence of precipitation of various liposomal compositions.

Table 6 shows treprostinil-, MRE-269-, Iloprost- and MPS-liposomal compositions have >80% EE, regardless of the types of weak acid salt used for drug loading. However, only treprostinil-liposomal compositions show the reduced burst release (less than 60% of the treprostinil is released within 2 hours from the time of administration) and extended IVR profile (more than 80% of the treprostinil is released more than 2 hours to within 72 hours (i.e. 12 hr) from the time of administration).

Figure 3A:
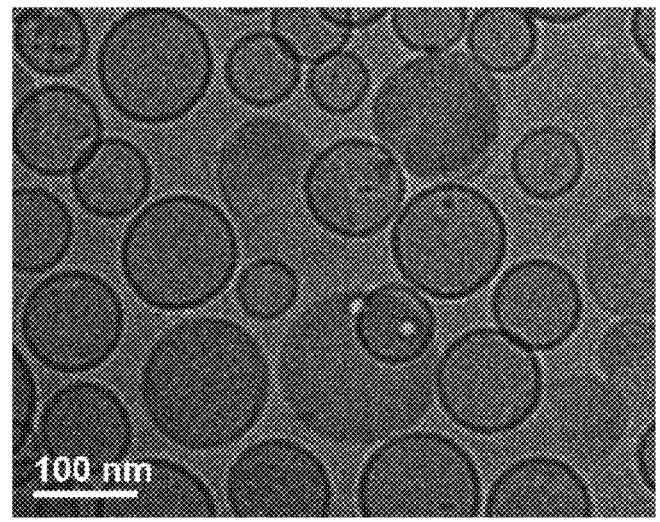
FIG. 3A to FIG. 3C are electron microscopic images showing the presence or absence of precipitation in the internal aqueous medium of the treprostinil-liposomal compositions (FIG. 3A and FIG. 3C) and methylprednisolone (MPS)-liposomal composition (FIG. 3B).
Figure 3B:
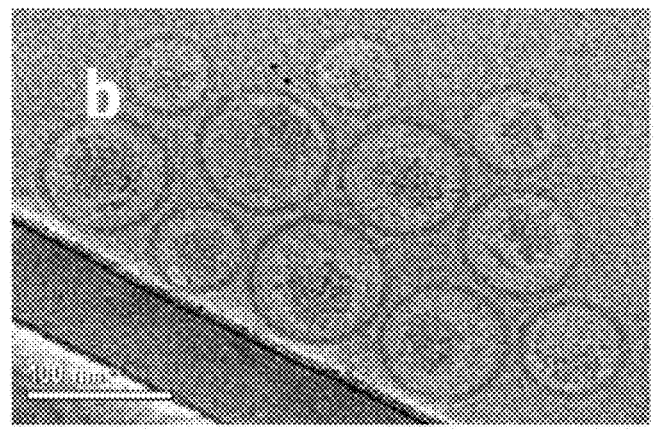
Figure 3C:
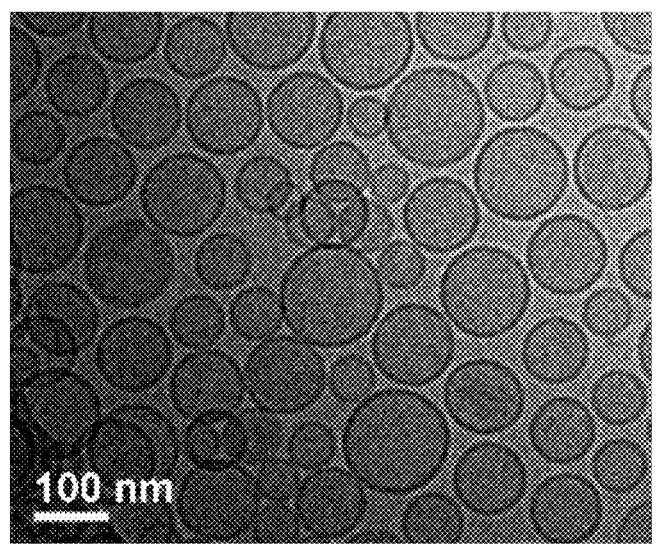

FIG. 3B illustrates the presence of precipitate in the internal aqueous medium of MPS-liposomal composition, whereas the internal aqueous medium of treprostinil-liposomal composition is substantially free of precipitation (FIG. 3A and FIG. 3C). Without being bound by any particular theory, it is believed the drug release from MPS-liposomal composition is prolonged or extended due to the presence of precipitation between MPS and calcium in the internal aqueous medium for a longer period of time. Hence, MPS could not be released completely from the precipitation to achieve the therapeutically effect.

Example 6. The IVR Profile of Treprostinil Liposomal Compositions with Different T/P Ratios Liposomal compositions comprising HSPC:Cholesterol:PEG2000-DSPE at a molar ratio of 3:2:0.075 (phospholipid of 8.59 mg/mL) were prepared according to the procedures outlined in Example 1. The mean particle size of liposome was 100-140 nm or 180-200 nm (marked with **) and PdI was less than 0.20. Treprostinil (TRE) was loaded into the liposomal composition using calcium acetate ($Ca(AC)_2$), sodium acetate (NaAC), sodium bicarbonate (NaBic) or lysine.

The IVR profile of the treprostinil-liposomal compositions were assessed using the procedures described in Example 1.

Results:

Table 7 shows the physicochemical characterization and IVR profile of treprostinil liposomal compositions with various T/P ratio.

TABLE 6

| Drug | Internal salt | L + F (mg/mL) | EE (%) | T/P ratio (w/w) | Precipitate | Release (%) in SLF (Reverse dialysis) | | | | | | | |
|---|---|---|---|---|---|---|---|---|---|---|---|---|---|
| | | | | | | 0 h | 2 h | 4 h | 8 h | 12 h | 24 h | 48 h | 72 h |
| TRE | 200 mM $Ca(AC)_2$ | 1.10 | 93.4 | 0.120 | No (FIG. 3A) | 0 | 28.6 | 48.6 | 79.9 | 83.0 | 92.0 | N.A. | N.A. |
| | 400 mM NaAC | 1.01 | 91.0 | 0.107 | No (FIG. 3C) | 0 | 31.1 | 46.7 | 75.8 | 87.3 | N.A. | N.A. | N.A. |
| | 400 mM NaBic | 0.99 | 97.6 | 0.112 | No | 0 | 26.3 | 47.4 | 72.2 | 82.8 | N.A. | N.A. | N.A. |
| MRE-269 | 200 mM $Ca(AC)_2$ | 1.09 | 99.4 | 0.126 | — | 0 | 85.9 | 82.4 | N.A. | N.A. | N.A. | N.A. | N.A. |
| | 400 mM NaAc | 1.54 | 94.8 | 0.170 | — | 0 | 79.6 | 83.4 | N.A. | N.A. | N.A. | N.A. | N.A. |
| | 400 mM NaBic | 1.12 | 92.1 | 0.120 | — | 0 | 100.0 | N.A. | N.A. | N.A. | N.A. | N.A. | N.A. |
| Iloprost | 400 mM NaAC | 0.94 | 82.5 | 0.090 | — | 0 | 86.9 | 87.5 | N.A. | N.A. | N.A. | N.A. | N.A. |
| | | 1.32 | 82.3 | 0.126 | — | 0 | 86.0 | 87.5 | N.A. | N.A. | N.A. | N.A. | N.A. |
| | 200 mM $Ca(Ac)_2$ | 0.93 | 94.2 | 0.102 | — | 0 | 88.8 | 93.0 | N.A. | N.A. | N.A. | N.A. | N.A. |
| | | 1.39 | 93.2 | 0.151 | — | 0 | 79.7 | 85.5 | N.A. | N.A. | N.A. | N.A. | N.A. |
| | | 1.50 | 92.6 | 0.162 | — | 0 | 90.6 | N.A. | N.A. | N.A. | N.A. | N.A. | N.A. |
| MPS | 200 mM $Ca(AC)_2$ | 0.75 | 92.1 | 0.070 | Yes (FIG. 3B[b]) | 0 | 1.6 | N.A. | N.A. | N.A. | 19.7 | 25.7 | 28.4[a] |

[a] The data was calculated by nature log fitting *release (%) = 7.5037 × Ln(time, hr) − 3.699
[b] FIG. 3B is extracted from Y. Avnir et al., Fabrication Principles and Their Contribution to the Superior In Vivo Therapeutic Efficacy of Nano-Liposomes Remote Loaded with Glucocorticoids, October 2011 | Volume 6 | Issue 10.

TABLE 7

| Internal salt | [TRE] (mg/mL) | EE (%) | T/P ratio (w/w) | Release (%) in SLF (Reverse dialysis) | | | | | |
|---|---|---|---|---|---|---|---|---|---|
| | | | | 0 h | 2 h | 4 h | 8 h | 12 h | 24 h |
| 400 mM NaAC | 0.36 | 96.8 | 0.041 | 0 | 36.0 | 73.0 | 83.0 | N.A. | N.A. |
| | 0.58 | 94.3 | 0.064 | 0 | 24.0 | 63.0 | 81.0 | N.A. | N.A. |
| | 1.06 | 89.1 | 0.110 | 0 | 20.8 | 39.9 | 69.0 | 85.5 | 89.6 |
| | 1.01 | 91.0 | 0.107 | 0 | 31.1 | 46.7 | 75.8 | 87.3 | N.A. |
| 200 mM Ca(Ac)$_2$ | 0.59 | 99.8 | 0.069 | 0 | 30.2 | 67.0 | 76.2 | 77.0 | 89.0 |
| | 1.10 | 93.4 | 0.120 | 0 | 28.6 | 48.6 | 79.9 | 83.0 | 92.0 |
| | 1.63 | 91.8 | 0.174 | 0 | 15.7 | 43.9 | 78.9 | 64.3 | 90.6 |
| | 1.66 | 94.5 | 0.183 | 0 | 13.0 | 33.2 | 61.5 | 63.9 | 97.8 |
| 400 mM NaBic | 0.40 | 99.9 | 0.047 | 0 | 46.3 | 72.7 | 94.3 | N.A. | N.A. |
| | 0.53 | 91.2 | 0.056 | 0 | 37.0 | 54.6 | 84.5 | N.A. | N.A. |
| | 0.99 | 97.6 | 0.112 | 0 | 26.3 | 47.4 | 72.2 | 82.8 | N.A. |
| | 1.57 | 96.7 | 0.177 | 0 | 20.5 | 40.0 | 64.5 | 74.6 | 94.1 |
| | 2.12** | 91.0 | 0.225 | 0 | 14.1 | 33.0 | 51.2 | 62.8 | 81.3* |
| 400 mM lysine | 0.49 | 100.0 | 0.057 | 0 | 28.5 | N.A. | 93.5 | N.A. | N.A. |
| | 1.03 | 100.0 | 0.120 | 0 | 6.8 | N.A. | 84.5 | N.A. | 89.6 |

*The data was calculated by nature log fitting(release (%) = 21.04 × Ln(time, hr) − 4.639)

Table 7 indicates that treprostinil-liposomal compositions (using sodium acetate, calcium acetate, sodium bicarbonate or lysine to establish the pH gradient) show reduced burst release (less than 60% of the treprostinil is released within 2 hours from the time of administration) and the extended IVR profile (more than 80% of the treprostinil is released more than 2 hours to within 72 hours (i.e. 8, 12, 24 hours) from the time of administration), provided the T/P ratio is equal to or greater than 0.035.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

What is claimed is:

1. A pharmaceutical composition, comprising:
   one or more liposome suspended in an external medium, said liposome comprising:
   (a) an external lipid bilayer, comprising at least one vesicle-forming phospholipid, wherein the vesicle-forming lipid consists of a mixture of a first phospholipid selected from the group consisting of phosphatidylcholine (PC), phosphatidylglycerol (PG), phosphatidylinositol (PI), phosphatidic acid (PA), phosphatidyethanolamine (PE), phosphatidylserine (PS) and any combination thereof and a second phospholipid selected from the group consisting of a PEG modified phospholipid, a positively charged or a negatively charged phospholipid, a charged lipid and any combination thereof; and
   (b) an internal aqueous medium, comprising treprostinil and a salt to provide a pH gradient between the internal aqueous medium and the external medium, said salt is a weak acid salt or an amino acid,
   wherein the weight ratio of treprostinil to the at least one vesicle-forming phospholipid is equal to or higher than about 0.035 and about less than 60% of the treprostinil is released within 2 hours after the administration of the pharmaceutical composition and more than 80% of the treprostinil is released more than 2 hours to about 72 hours after the administration of the pharmaceutical composition.

2. The pharmaceutical composition of claim 1, wherein the weight ratio of treprostinil to the at least one vesicle-forming phospholipid equal to or higher than about 0.041.

3. The pharmaceutical composition of claim 1, wherein the weight ratio of treprostinil to the at least one vesicle-forming phospholipid is equal to or higher than about 0.052.

4. The pharmaceutical composition of claim 1, wherein the weight ratio of treprostinil to the at least one vesicle-forming phospholipid is equal to or higher than about 0.056.

5. The pharmaceutical composition of claim 1, wherein the external lipid bilayer further comprising a sterol.

6. The pharmaceutical composition of claim 5, wherein the sterol is selected from the group consisting of cholesterol, cholesterol hexasuccinate, ergosterol, lanosterol, and any combination thereof.

7. The pharmaceutical composition of claim 1, wherein the weak acid salt is carboxylic acid salt or bicarbonate salt.

8. The pharmaceutical composition of claim 7, wherein the carboxylic acid salt is selected from the group consisting of formate, acetate, propionate, butyrate, isobutyrate, valerate, isovalerate, benzoate and any combination thereof.

9. The pharmaceutical composition of claim 8, wherein the acetate is sodium acetate, calcium acetate or any combination thereof.

10. The pharmaceutical composition of claim 1, wherein the amino acid is a polar amino acid.

11. The pharmaceutical composition of claim 10, wherein the polar amino acid is a neutral polar amino acid.

12. The pharmaceutical composition of claim 10, wherein the polar amino acid is a basic polar amino acid.

13. The pharmaceutical composition of claim 1, wherein more than 80% of the treprostinil is released more than 2 hours to about 48 hours after the administration of the pharmaceutical composition.

14. The pharmaceutical composition of claim 1, wherein more than 80% of the treprostinil is released more than 2 hours to 24 hours after the administration of the pharmaceutical composition.

15. The pharmaceutical composition of claim 1, wherein the internal aqueous medium is substantially free of precipitation.

16. The pharmaceutical composition of claim 1, wherein the pharmaceutical composition is substantially free of a detergent or an ionophore.

17. The pharmaceutical composition of claim 1, wherein the first phospholipid is selected from HSPC, DSPC, DPPC, DMPC or any combination thereof and the second phospholipid selected from DSPG, DPPG, DMPG, PEG-DSPE, or any combination thereof.

18. The pharmaceutical composition of claim 1, wherein the first phospholipid is selected from HSPC, DSPC, DPPC, DMPC or any combination thereof and the charged lipid is stearylamine, 1,2-dioleoyl-3-trimethylammonium-propane (DOTAP), 3ß-[N—(N',N'-dimethylaminoethane)-carbamoyl]cholesterol (DC-Cholesterol), $N^4$-Cholesteryl-Spermine (GL67), dimethyldioctadecylammonium (DDAB), 1,2-di-O-octadecenyl-3-trimethylammonium propane (DOTMA), ethylphosphocholine (ethyl PC) or any combination thereof.

* * * * *